(12) United States Patent
Suturin et al.

(10) Patent No.: US 12,588,923 B2
(45) Date of Patent: Mar. 31, 2026

(54) DEVICE FOR PERFORMING A COSMETIC OR MEDICAL PROCEDURE

(71) Applicant: Aliform Inc., Dover, DE (US)

(72) Inventors: Victor Suturin, Aachen (DE); Mikhail Soutorine, Hughesdale (AU)

(73) Assignee: Aliform Inc., Dover, DE (US)

( * ) Notice: Subject to any disclaimer, the term of this patent is extended or adjusted under 35 U.S.C. 154(b) by 521 days.

(21) Appl. No.: 17/626,306

(22) PCT Filed: Jul. 10, 2020

(86) PCT No.: PCT/EP2020/069612
§ 371 (c)(1),
(2) Date: Jan. 11, 2022

(87) PCT Pub. No.: WO2021/009063
PCT Pub. Date: Jan. 21, 2021

(65) Prior Publication Data
US 2022/0265297 A1 Aug. 25, 2022

(30) Foreign Application Priority Data

Jul. 12, 2019 (AU) ................................ 2019902470

(51) Int. Cl.
*A61B 17/32* (2006.01)
*A61B 17/00* (2006.01)
(52) U.S. Cl.
CPC .... *A61B 17/32* (2013.01); *A61B 2017/00761* (2013.01); *A61B 2017/00867* (2013.01); *A61B 2017/320044* (2013.01)
(58) Field of Classification Search
CPC .......... A61B 17/32; A61B 2017/00761; A61B 2017/00867; A61B 2017/320044;
(Continued)

(56) References Cited

U.S. PATENT DOCUMENTS 3,791,387 A * 2/1974 Itoh ........................ A61B 17/29
606/113
11,013,527 B1 5/2021 Podmore et al.
(Continued)

FOREIGN PATENT DOCUMENTS

EP 3826558 A1 6/2021
WO 2020023412 A1 1/2020

OTHER PUBLICATIONS

International Search Report and Written Opinion for Application No. PCT/EP2020/069612 mailing date Nov. 4, 2020, 11 pgs.

*Primary Examiner* — Brooke Labranche
*Assistant Examiner* — Rachael L Geiger
(74) *Attorney, Agent, or Firm* — Seed Intellectual Property Law Group LLP

(57) ABSTRACT

A device for performing a cosmetic or medical procedure and methods of operating such a device are usable for treating fibrous adhesions, such as those implicated in the formation of cosmetic or medical conditions including but not limited to cellulite. Embodiments of the disclosure have been particularly developed for targeting and disrupting fibrous adhesions to restore or improve normal physiological tissue function and/or aesthetic appearance. In at least one embodiment, the device comprises an elongate body and one or more user controllable breaking means. Each breaking means is actuatable to move between a retracted position in which the breaking means is in a collapsed configuration and an operative position in which the breaking means is in an expanded configuration suitable to break a strand of fibrous material or fibrous connective tissue.

12 Claims, 10 Drawing Sheets

(58) Field of Classification Search
CPC ........... A61B 2017/00358; A61B 2017/00871;
A61B 17/00234; A61B 17/32056; A61B
17/320016; A61B 17/32093; A61B
2017/32006; A61B 17/221; A61B
2017/2212; A61F 2/2442; A61F 2/2445;
A61F 2/2448; A61F 2/2451; A61F
2/2463; A61F 2/2466
See application file for complete search history.

(56) References Cited

U.S. PATENT DOCUMENTS

| | | | |
|---|---|---|---|
| 11,974,767 B2 | 5/2024 | Makower et al. | |
| 12,023,063 B2 | 7/2024 | Podmore et al. | |
| 2004/0204734 A1 | 10/2004 | Wagner et al. | |
| 2006/0241672 A1 | 10/2006 | Zadini et al. | |
| 2008/0009875 A1 | 1/2008 | Sankaran et al. | |
| 2008/0009877 A1* | 1/2008 | Sankaran ........... | A61B 17/1617 |
| | | | 604/506 |
| 2010/0228182 A1 | 9/2010 | Clark, III et al. | |
| 2012/0130164 A1* | 5/2012 | Palese ................... | A61B 17/52 |
| | | | 600/104 |
| 2022/0265297 A1* | 8/2022 | Suturin ............ | A61B 17/00234 |
| 2023/0389951 A1 | 12/2023 | Makower et al. | |

* cited by examiner

DEVICE FOR PERFORMING A COSMETIC OR MEDICAL PROCEDURE

BACKGROUND

Technical Field

The present disclosure relates to a device for performing a cosmetic or medical procedure and to methods of operating such a device. Suitably, the present disclosure relates to a device for treating fibrous adhesions, such as those implicated in the formation of cosmetic or medical conditions including but not limited to cellulite. Embodiments of the disclosure have been particularly developed for targeting and disrupting fibrous adhesions to restore or improve normal physiological tissue function and/or aesthetic appearance and will be described hereinafter with reference to this application. However, it will be appreciated that the disclosure is not limited to this particular field of use.

Description of the Related Art

Connective tissue plays an important role in ensuring structural integrity of body tissues and organs. In some instances, connective tissue structures can form fibrous adhesions, which become excessively stiff and hinder normal physiological tissue function manifesting in cosmetic and/or medical conditions. The causes for abnormal stiffening range from genetic predisposition, trauma-related impact to metabolic imbalances, and others. For example, abdominal surgery commonly results in formation of fibrous adhesions due to surgery-related trauma and subsequent tissue healing responses. In another example, skin transplants often exhibit abnormally higher stiffness post-transplantation due to scar tissue formation, which limits free movement of the skin-graft. Similarly, contracture scars which can form because of trauma are also known to impair normal tissue function.

In cases where connective tissue in the form of fibrous adhesions causes compression of blood vessels or nerves, serious health consequences can be suffered.

Carpal tunnel syndrome is a common example of nerve compression by fibrous adhesions within a connective tissue band, which becomes stiff.

Similarly, compartment syndrome is a serious medical condition with debilitating consequences, which occurs following trauma to skeletal muscle. Treatment involves relief of pressure by targeting the fibrous adhesions in the connective tissue enclosing the muscle.

In a further example, a combination of genetic and local tissue metabolic factors can cause fibrous adhesions leading to skin connective tissue septae to tighten, causing cellulite—an cosmetic skin condition affecting more than 90% of adult women.

Cellulite occurs when the fibrous connective tissue adhesions (also known as fibrous septae) beneath the skin become stiff, and together with bulging fat tissue cause an unaesthetic dimple-like, lumpy appearance, most commonly on the buttocks and thighs of a person.

Connective tissue adhesions are a normal part of skin anatomy. However, in the conditions described above, these adhesions become fibrous and undesirably stiff. In cellulite, for example, and in particular when surrounded by excessive fat, these fibrous adhesions cause the formation of skin depressions or "dimples."

Similarly, fibrous adhesions are known to affect the appearance and texture of skin after liposuction, during pregnancy, or during injury/trauma recovery as part of internal scarring.

Depending on the indication, surgical treatments of fibrous adhesions involve different forms of disruption, either via cutting, stretching, burning using a laser, ultrasound and other. In the case of cellulite treatment, one effective method called minimally-invasive subscission involves either cutting the fibrous adhesions, or burning them with a laser. In those approaches, the goal is to relieve the pulling force of the stiffened connective tissue, which contributes to the formation of skin dimples.

One method of treating cellulite involves the insertion and manipulation of a loop saw under the skin to cut the fibrous adhesions.

A more delicate method involves stabilizing a portion of the skin affected with cellulite using a vacuum chamber, followed by subscission performed using a motorized micro-blade.

Disadvantages of these treatment methods include undesirable tissue trauma due to indiscriminate cutting or burning of the tissue, which causes potentially detrimental damage to functionally important structures like blood vessels and nerves. Consequently, side effects are often observed in a form of excessive bleeding, bruising, additional scar formation and/or nerve damage. Heightened risks of complications present serious hurdles for both doctors and their patients.

Another method of treating fibrous adhesions associated with cellulite involves the insertion of a fork-like cutting instrument under the skin, which is then pushed against the fibrous adhesions to cut them.

A disadvantage of this method is again the high risk of tissue trauma due to the difficulty in controlling the forward motion of the instrument into the fibrous adhesion without damaging tissue within the vicinity of the adhesion. In addition, placing a cutting fork under the skin requires a large entry point, further increasing the invasiveness of this treatment method.

There is a need in the art for improved devices and methods useful for treating cosmetic or medical conditions associated with fibrous adhesions.

BRIEF SUMMARY

The present disclosure provides improved devices for cosmetic or medical treatment of fibrous adhesions, which minimize undesirable side effects arising from indiscrete tissue damage.

One of the safest known approaches to connective tissue dissection involves mechanical stretching using blunt surgical instruments. For example, to isolate a blood vessel or nerve entrapped by connective tissue, the connective tissue can be disrupted by pulling it apart through the application of mechanical force using blunt forceps or the blunt sides of a pair of scissors (known as "blunt scissors dissection technique"). Using this well-known technique, connective tissue is disrupted while the entrapped blood vessels and nerves can be preserved. This is possible due to the different stress/strain properties of blood vessels and nerves compared to the connective tissue, and in particular compared to the fibrous adhesions therein, with the former two being significantly more elastic than the latter.

In a first aspect of the present disclosure, there is provided a device for performing a cosmetic or medical procedure comprising an elongate body and one or more user controllable breaking means that are positioned within or on the elongate body, wherein the breaking means is actuatable to move between a retracted position and an operative position. When in the retracted position, the breaking means is in a collapsed configuration and when in the operative position, the breaking means is in an expanded configuration suitable to break a strand of fibrous material.

While the devices of the present disclosure are suitable to be used in a plurality of procedures targeting fibrous adhesions in various parts of a patient's body, the devices according to the here-described embodiments of the disclosure are particularly suited for performing a cosmetic or medical procedure, wherein the procedure is a treatment, preferably a minimally invasive treatment, of fibrous adhesions associated with medical or cosmetic skin conditions, including cellulite, wrinkles, acne, burns or depressed skin-grafts; surgical treatment; trauma; scarring; pregnancy; and/or nerve or blood vessel compression, including carpal tunnel syndrome or compartment syndrome. In at least one embodiment, the device is particularly suited for treating fibrous adhesions causing cellulite, especially on the legs, and particularly the thighs.

In the context of the present disclosure, the breaking means is configured to break a strand of fibrous material by tensioning or stretching the strand until complete or partial rupture of a fibrous adhesion. Suitably, the breaking means does not cut the strand of fibrous tissue, thus reducing the risk of indiscreetly cutting into surrounding tissue, blood vessels and/or nerves.

In this specification, the term "fibrous material" refers to material comprising organic or inorganic fibers, such as fibrous connective tissue.

The elongate body may be hollow. Suitably, the elongate body is a hollow cannula.

The elongate body may be configured to be pushed between layers of tissue.

The device may include more than one breaking means.

The breaking means may be positioned within or on the elongate body.

The multiple breaking means may be of different shapes and sizes when co-localized on the elongate body.

In at least one embodiment of the disclosure, the breaking means is slidable within or on the elongate body such that the breaking means slides within or on the elongate body when moving from the retracted position into the operative position.

The elongate body may comprise a sliding member slidingly movable within or on the elongate body. The breaking means may be attached to the sliding member.

In some embodiments, the breaking means is positioned within the elongate body and the elongate body has an opening through which the breaking means extends when moving into the operative position.

The elongate body and/or the sliding member may be configured such as to restrict rotation of the breaking means relative to the elongate body when the breaking means is in the expanded configuration. This may reduce misalignment of the breaking means to the strand of fibrous connective tissue during the transition between the retracted and operative positions.

The breaking means may be a pair of arms that are transitionable between the retracted position and the expanded position. For example, the pair of arms may adopt a Y-shape configuration in the expanded position and an I-shape configuration in the retracted position.

The breaking means may be a piece of wire. Suitably, the breaking means is a loop of wire. A region of the loop of wire may be shaped to form a tip to guide the breaking means under the skin of a patient. In some of these embodiments, the breaking means is positioned within the elongate body and the elongate body has an opening through which the breaking means extends when moving into the operative position.

The breaking means may be arranged in a multi-part configuration, comprising several breaking elements jointly forming the breaking means. For example, a generally loop-shaped breaking means may comprise at least two parts, preferably two breaking elements, optionally made of wire or of a rigid material, for example a non-flexible material, wherein the at least two breaking elements are hingedly and/or pivotally connected to each other such as to provide the breaking means with the required flexibility to move between the retracted position and the operative position. Further, the hinged and/or pivoted connections between the breaking elements may serve to provide the breaking means with a predetermined flexibility suitable to allow for selective breakage of fibrous adhesions but to avoid or at least minimize indiscreet tissue damage during operation of the device.

The breaking means may be one or more individual wires, either connected or individually arranged such as to allow for combined or individual actuation.

In at least one embodiment of the present disclosure, the breaking means is a wire, which, in the expanded configuration, assumes the shape of a hoop, a half-hoop, an oval, an ellipse, a diamond, a rectangle, or a square or assumes a leaf-like shape. However, it can be appreciated that the breaking means can adopt other shapes.

The breaking means may be a loop assuming a variety of shapes in the expanded configuration, including the above-described shapes. For example, a loop having a smoother profile may be used to break the strands of fibrous connective tissue in a more gradual manner compared to a loop having a profile comprising abrupt undulations.

The breaking means may be positioned on an external surface of the elongate body. In this embodiment, the elongate body may be contoured with grooves to receive the breaking means such that the breaking means sit flush with the surface of the elongate body in the retracted position.

The breaking means may expand in several dimensions when transitioning from the collapsed configuration to the expanded configuration. Suitably, the breaking means expands along one plane when transitioning from the collapsed configuration to the expanded configuration.

The breaking means may have a blunt end. Suitably, the breaking means has a pinched end. This minimizes the risk of the breaking means causing tissue trauma when it is inserted under the skin of a patient. Suitably, the breaking means forms a leaf-like shape in its expanded configuration. The pinched end may form the tip of the leaf-like shape. The breaking means may constitute two half-leaves, with an end being attached to the distal end of the elongate body and another end being attached to proximal end of the sliding member.

The breaking means may be movable, preferably slidably movable, in discrete increments, between the retracted position and the operative position such that expansion of the breaking means into the expanded configuration occurs in corresponding increments. This incremental expansion or retraction of the breaking means allows the operator to adjust the reach of the breaking means during operation of the device.

The breaking means may have a non-cutting edge. Suitably, the breaking means is blunt. This enables the breaking means to move under the skin of a patient without perforating, puncturing, or damaging the tissue layers or blood vessels and nerves in the vicinity of the fibrous adhesion to be broken, while tensioning strands of fibrous tissue.

The breaking means may be made of any suitable material that has sufficient strength to break strands of fibrous connective tissue.

The breaking means may be made of any suitable material that can repeatedly transition between the collapsed and expanded configurations without fracturing. Suitably, the material does not have a fatigue limit. Appropriate materials include shape memory alloys such as nitinol, ductile materials such as copper, iron, or steel, and alloys thereof.

Other suitable materials include metals such as titanium and silver and alloys thereof, polymers such as nylon, polyethylene, polymethylmethacrylate, polycarbonate, and composites thereof.

In at least one embodiment, the breaking means may be dental wire.

The breaking means may have a natural expanded configuration, i.e., be biased towards the expanded configuration. In this embodiment, the breaking means would be placed be under tension on or within in the elongate body.

The breaking means may have a natural collapsed configuration, i.e., be biased towards the collapsed configuration. In this embodiment, the breaking means would have to be actively moved into the expanded configuration. For example, a region of the breaking means may be connected to a tether such that pulling or pushing the tether transitions the breaking means between the collapsed and expanded configuration. In another example, the breaking means may be moved into the expanded configuration by compressing the breaking means.

The breaking means may be detachable from the elongate body. In one embodiment, the breaking means is adapted for single use.

All embodiments of the above-described device may comprise a plurality of breaking means.

The device may include a handle. In one embodiment, the handle is separate to the elongate body. In another embodiment, the handle is part of the elongate body. The breaking means of the device may be actuatable via a mechanism in a handle or manually by an operator's hand.

The breaking means may be actuatable to move between the retracted position and the operative position through an open end of the elongate body.

The open end of the elongate body may have a profile that does not puncture or cut the layers of tissue. Suitable profiles include a blunt end having a rounded or a flat profile.

The elongate body may be shaped to facilitate manipulation around the contours of a body part. In one embodiment, the elongate body is straight. In another embodiment, the elongate body is curved.

The elongate body may have a variety of cross-sectional profiles, which may be radially symmetrical or asymmetrical. Suitable cross-sectional profiles include circular, oval, polygonal and rectangular profiles. In one embodiment, the elongate body has a radially asymmetrical cross-sectional profile such as an oval or flattened profile. This allows a user to determine the orientation of the breaking means without sighting the breaking means, for example, when under the skin of a patient. In another embodiment, the surface of the elongate body may be marked to assist a user in determining the orientation of the breaking means.

The elongate body may be deformable to be retained in a desired shape permanently or temporarily. For example, the elongate body may permanently remain in a set form after being deformed into this form. Alternatively, the elongate body may be biased towards a default form and, therefore, will revert to this default form over time after being deformed.

The elongate body may be a component of a known device, such as a liposuction cannula, a laparoscopic cannula, or a body of an endoscope adapted for use in the device of the present disclosure.

The elongate body may contain an illuminating element to provide a visual navigation aid when the device is being maneuvered within body orifices.

The elongate body may be made from a material or have a suitable coating or emit a signal via a transmitter or combinations thereof, all of which provide contrast enhancement during operation of the device such as to allow for the device to be more readily visualized using imaging methods such as ultrasound, magnetic resonance imaging, photoacoustic imaging, PET, CT, etc., in order to facilitate maneuvering the device.

The elongate body may be made of a material that has sufficient strength and rigidity to separate adjacent layers of tissue when inserted under the skin of the patient without puncturing or cutting the tissue. Suitable materials include steel, or ductile materials such as copper or iron.

The elongate body may be made of a material, which allows it to bend and be retained in a desired shape.

Suitable materials include steel, or ductile materials such as copper or iron, or any alloys thereof.

The elongate body may include a stop that engages the breaking means to prevent the breaking means from unintentionally being released from the elongate body. The stop may be positioned in the lumen of the elongate body.

As noted earlier, the elongate body may have an opening through which the breaking means extends when moving into the operative position. The opening on the elongate body may be located on the body wall.

The opening on the elongate body may be located at a distal end of the elongate body. Suitably, the opening on the elongate body is located at the tip of the elongate body.

The device may include an actuator to move the breaking means from the retracted to the operative position and vice versa.

The actuator may engage the breaking means.

The actuator may be mechanically, magnetically or electronically operated. Other types of actuator, such as hydraulic or pneumatic may also be used.

In at least one embodiment, the actuator is a button, or slider that is operatively engageable to the breaking means via a member extending through the elongate body. Operation of the button or slider may cause movement of the breaking means between the retracted and operative positions. In at least one embodiment, the actuator is the member extending through the elongate body. Suitably, the member is slidable within the elongate body.

In at least one embodiment, the actuator is engageable to an end of the breaking means. Suitably, ends of the breaking means are anchored to the actuator.

In another embodiment, the actuator and breaking means have complementary mating ends to engage each other.

The actuator may be located on the handle or the elongate body.

Another example of an actuator includes a spring-loaded mechanism to cause movement of the breaking means between the retracted and operative position. This mechanism may be operated in response to an electrical, mechanical, or magnetic actuation signal. In some embodiments, the spring-loaded mechanism may be configured for single use actuation to cause movement of the breaking means from the retracted position to the operative position. In other embodiments, the spring-loaded mechanism may be operable to cause movement of the breaking means reversibly between the retracted position and the operative position.

In another example, the actuator includes a spring biased hydraulic or pneumatic mechanism to cause movement of the breaking means between the retracted and operative positions.

In another example, the actuator may include a screw thread to translate rotational movement of an actuator into movement of the breaking means between the retracted and operative position.

In another example, the actuator may include an electronic mechanism that triggers a repeated forward-backwards motion of the cannula body and/or the breaking means in the operative state to aid breaking of the fibrous material.

In another example, the breaking means and/or the elongate body may act as a vibrating/pulsatile element controlled by the electronic mechanism to assist in the breaking/disruption of the fibrous adhesions. For example, the breaking means and/or the elongate body may comprise an ultrasonic component. Suitably, the electronic mechanism is located in the handle.

In another example, the device includes a plurality of breaking means that are actuatable to move in a scissoring motion relative to each other along the axis of the cannula body to aid breaking of the fibrous material.

The device may be sealed within a package.

The device in the sealed package may be sterile.

In a second aspect, the present disclosure relates to a method of operating a device comprising an elongate body having a proximal end and a distal end, and one or more breaking means retained in a retracted position within or on the elongate body. The method comprises the steps of positioning the elongate body at a target location and actuating the breaking means to move from a retracted position to an operative position, wherein the breaking means transitions from a collapsed configuration into an expanded configuration suitable to break a strand of fibrous material.

Suitably, the method is for operating the device according to the first aspect of the disclosure.

Actuating the breaking means may include extending the breaking means through an opening at the distal end of the elongate body.

Actuating the breaking means may include moving the breaking means from the retracted position to the operative position through an opening on the elongate body.

In an embodiment, the method further comprises the step of actuating the breaking means to move from the operative position to a retracted position. For example, the device may be maneuvered into position, and the actuator operated to move the breaking means from the retracted position to the operative position, then the device is maneuvered to partially or completely break a strand of fibrous material by tensioning the fibrous material to and/or past the point of rupture, and subsequently the actuator is operated to cause the breaking means to move from the operative position to the retracted position, to allow the device to be withdrawn without puncturing or cutting tissue in the vicinity of the fibrous material.

In a third aspect, the present disclosure relates to a method of operating a device comprising an elongate body having a proximal and a distal end, and a breaking means retained in a retracted position within or on the elongate body, including:

creating an entry point puncture;

inserting the breaking means in its retracted position through the entry point puncture and maneuvering the breaking means in its retracted position through tissue of the patient to a target location having a strand of fibrous connective tissue, wherein in its retracted position the breaking means adopts a collapsed configuration;

actuating the breaking means to transition into its operative position, in which the breaking means adopts an expanded configuration;

manipulating the device such as to break the strand of fibrous connective tissue using the breaking means; and actuating the breaking means to transition into its retracted position.

Suitably, the method is for operating the device according to the first aspect of the disclosure.

The method may include inserting the elongate body through the entry point puncture.

The step of inserting the elongate body through the entry point puncture may include actuating the device to move into the retracted position.

The method may include a step of bending the elongate body into a desired shape to facilitate maneuvering of the elongate body under the skin.

The target location may be located behind or in front of a strand of fibrous connective tissue.

The step of maneuvering the device, e.g., under the skin, may include moving the breaking means past a strand of fibrous connective tissue to be broken. In this embodiment, after actuation, the breaking means breaks the fibrous connective tissue by withdrawal the breaking means towards the entry point puncture.

Alternatively, the step of maneuvering the device, e.g., under the skin, may include positioning the breaking means in front of the fibrous connective tissue. In this embodiment, after actuation, the breaking means breaks the fibrous connective tissue by being pushed towards and against the fibrous connective tissue.

An advantage of breaking the fibrous connective tissue by a withdrawing (pulling) motion compared to an inserting (pushing) motion is that tissue damage is minimized by reducing the risk of puncturing or perforating tissue during the motion. This provides a safer treatment process.

The step of actuating the breaking means to move into the operative position may be performed via a number of ways including pushing the breaking means, manipulating a slider, activating a button that is in mechanical communication with the breaking means, or activating a switch that is in electrical communication with the breaking means.

The method may include withdrawing the breaking means through the puncture point.

The method may include withdrawing the elongate body through the puncture point.

The method may include using the breaking means to partially break or weaken the fibrous connective tissue, if desired, as opposed to breaking them completely.

One or more of the steps may be repeated during the procedure. This allows the operator to cut strands of fibrous connective tissue under different areas of the skin.

BRIEF DESCRIPTION OF THE SEVERAL VIEWS OF THE DRAWINGS

A preferred embodiment of the present disclosure is hereinafter described by way of example only, with reference to the accompanying drawings, wherein.

DETAILED DESCRIPTION

The present disclosure can be used in cosmetic and medical procedures associated with the treatment of fibrous adhesions. Suitably, the treatment is a minimally invasive treatment of fibrous adhesions. The treatment may be a treatment of fibrous adhesions associated with medical or cosmetic skin conditions, including cellulite, wrinkles, acne, burns or depressed skin-grafts; surgical treatment; trauma; scarring; pregnancy; and/or nerve or blood vessel compression, including carpal tunnel syndrome or compartment syndrome.

Figure 7:
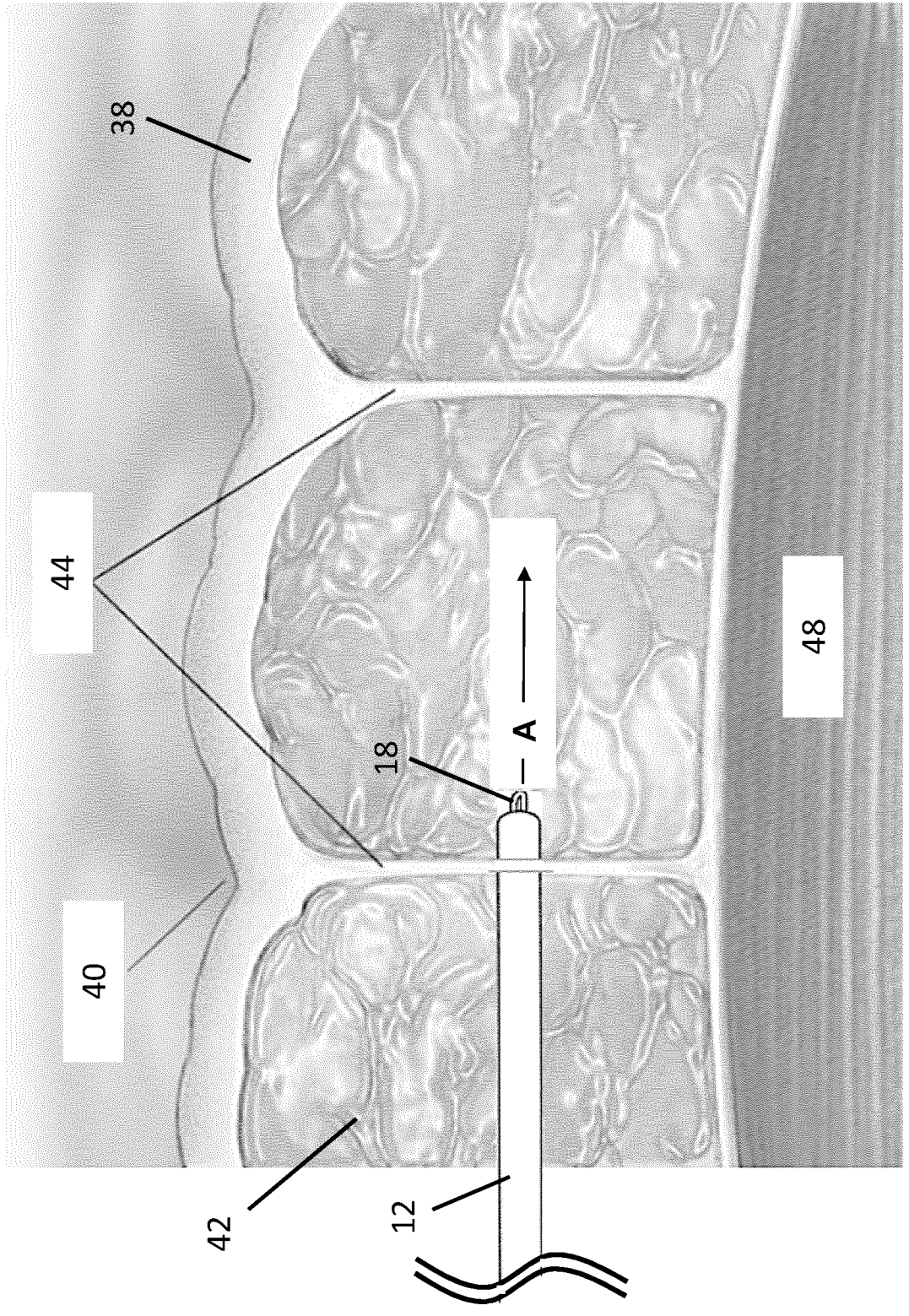
FIG. 7 is an illustration of a device according to one form of the present disclosure positioned at a target location under the skin of a patient in a retracted position.
Figure 8:
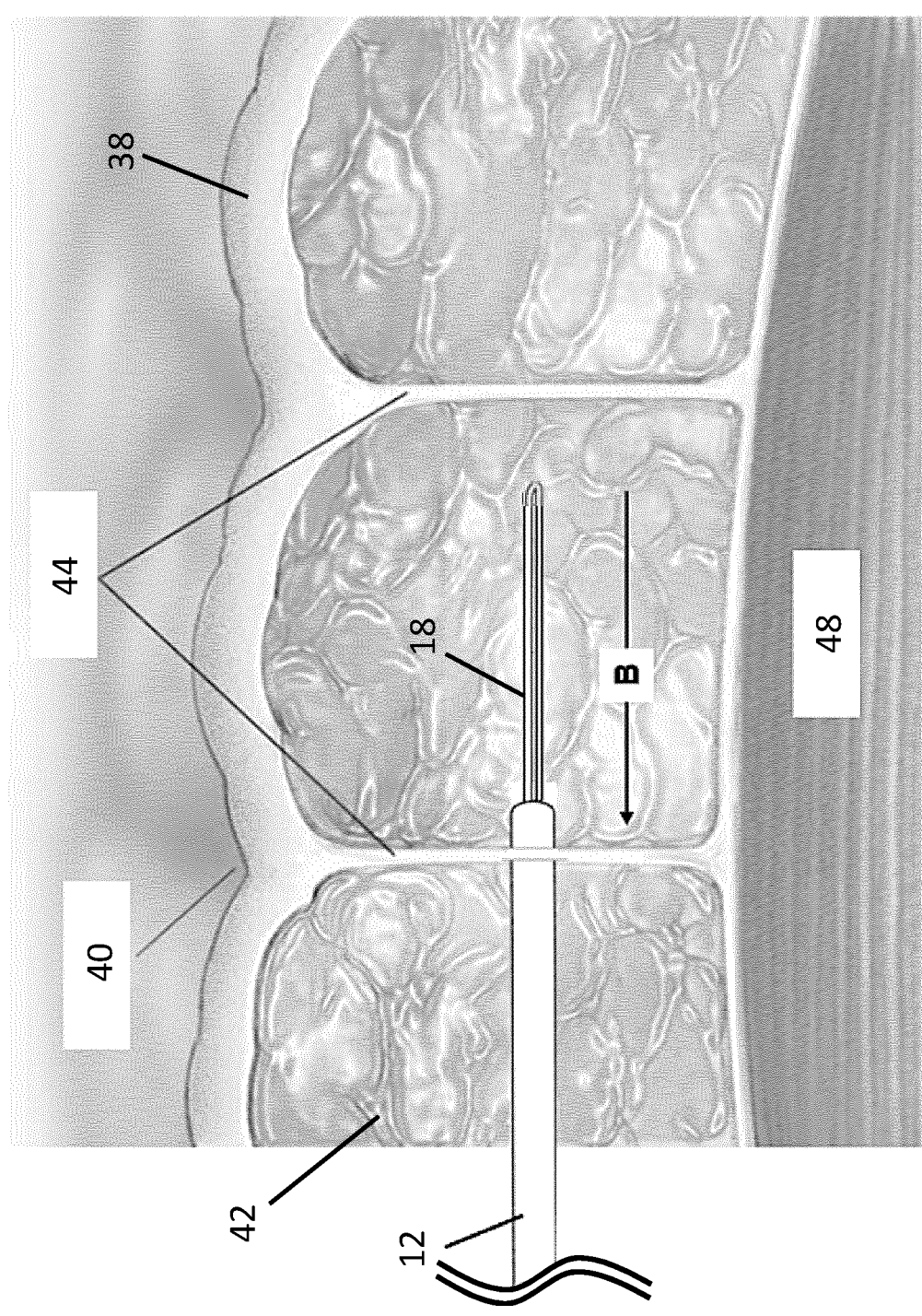
FIG. 8 is an illustration of the device in FIG. 7 positioned at a target location under the skin of a patient in an operative position.
Figure 9:
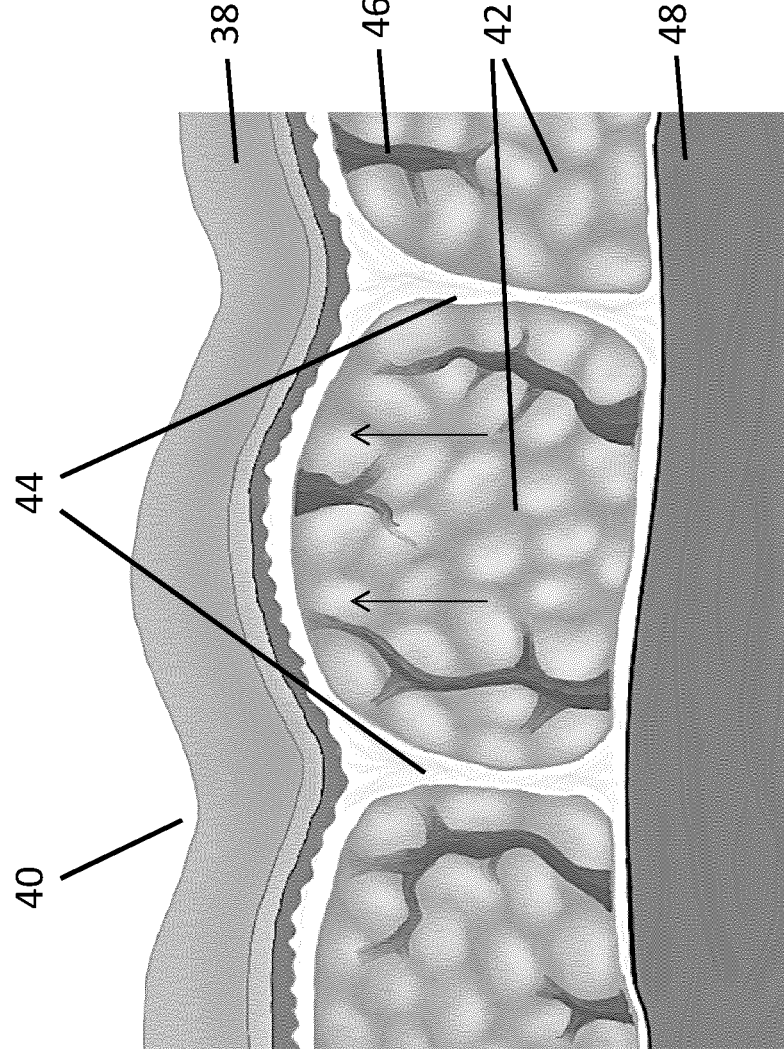
FIG. 9 is an illustration of the manifestation of cellulite in a person's skin.
Figure 10:
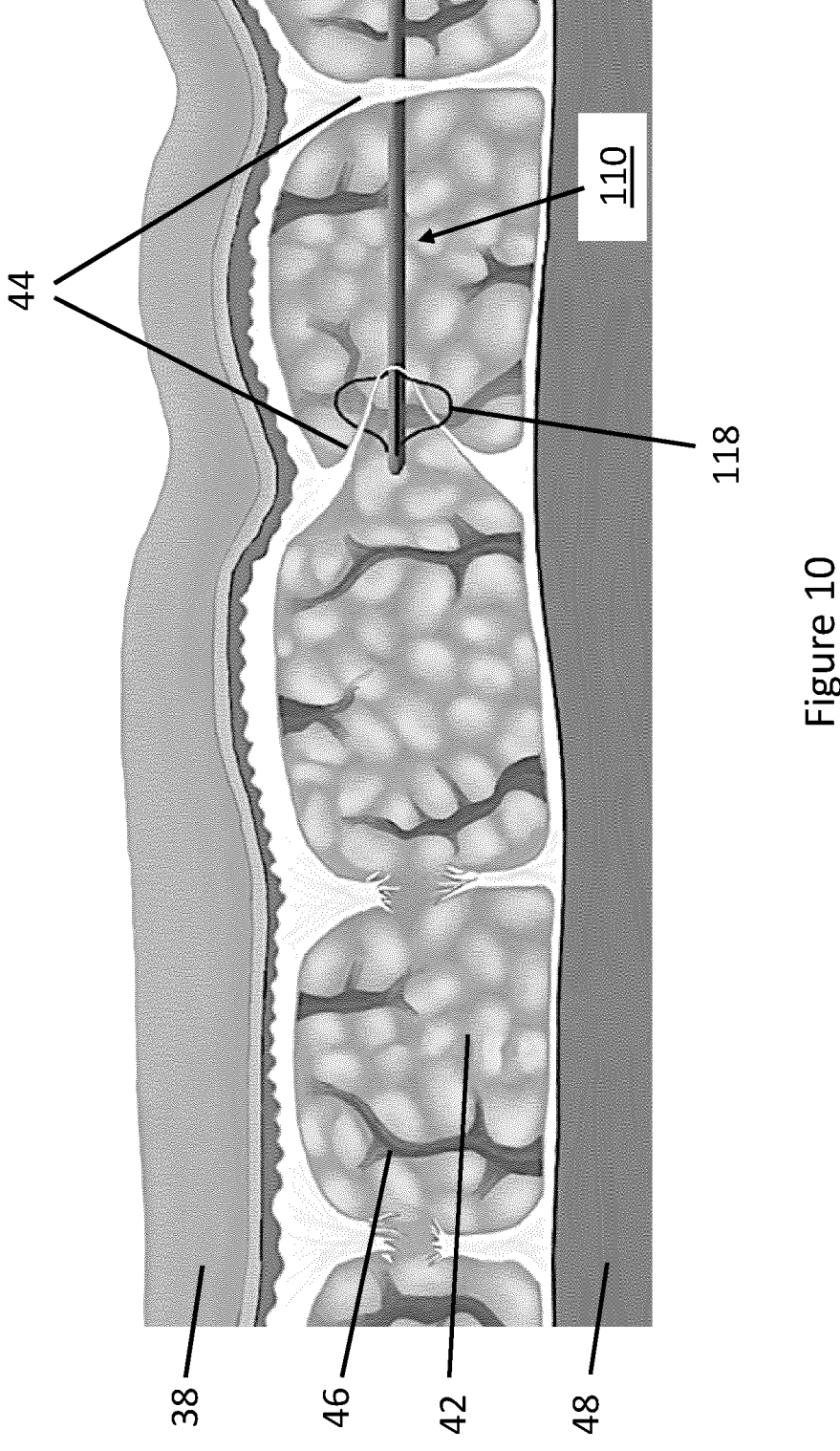
FIG. 10 is an illustration of the device of FIGS. 3B and 4B shown while being manipulated during a method of operation of the device such as to break strands of fibrous connective tissue using the breaking means.

In cosmetic procedures to remove the appearance of cellulite from the body of a patient, as well as in other conditions where fibrous adhesions contribute to formation of skin dimples such as for example after liposuction or pregnancy, the device of the present disclosure is used to rupture fibrous connecting tissue spanning the subcutaneous fat layer from the epidermis 36 to the muscle tissue layer 38 (see FIGS. 7 and 8).

The device of the present disclosure can also be used in skin grafting, namely pre- and post-transplantation to loosen fibrous connective tissue adhesions. It can also be used to target fibrous adhesions associated with abdominoplasty.

Figures 1A, 1B:
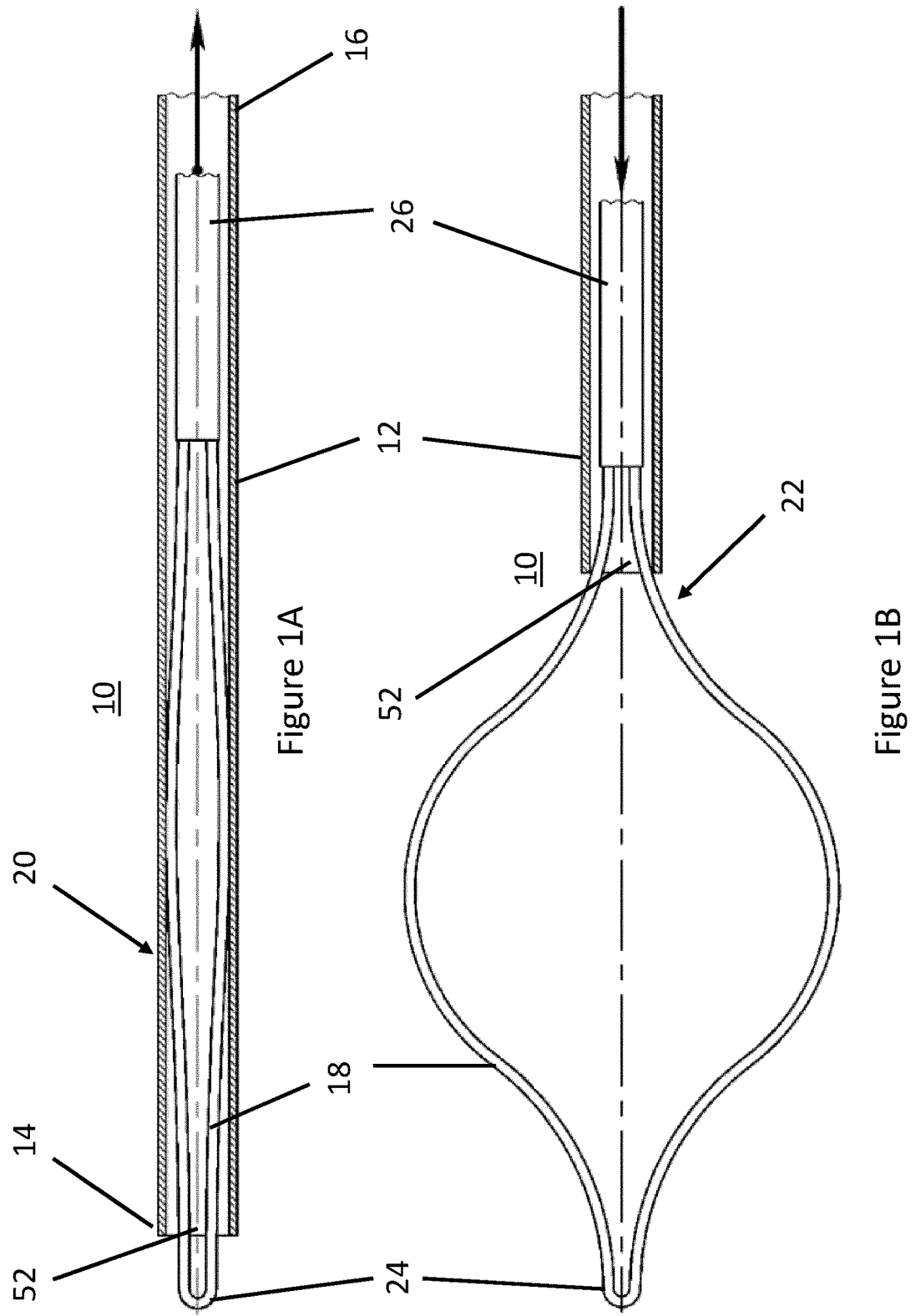
FIG. 1A is a cross-sectional side view of a device according to one form of the present disclosure in a retracted position.
FIG. 1B is a cross-sectional side view of the device in FIG. 1A in an operative position.

One embodiment of the device as defined by the disclosure is marked as device 10 in FIGS. 1A/B and 2A/B. The device 10 comprises an elongate body in the form of hollow cannula 12 configured to be pushed between layers of tissue, the hollow cannula 12 comprising a distal end 14 having an opening 52, 152, and a proximal end 16.

A user controllable breaking means, in the form of wire loop 18 is positioned within the hollow cannula 12. Suitably, the wire loop 18 does not possess a cutting edge to minimize the risk of the wire loop puncturing tissue in the vicinity of the strand of fibrous tissue. It can be appreciated that in other embodiments, the cannula 12 is not inserted under the skin of the patient but positioned at the entrance of a puncture site to introduce the wire loop 18 under the skin of the patient.

The wire loop 18 is actuatable to move between a retracted position 20 and an operative position 22. In the retracted position 20, the wire loop 18 is housed within the hollow cannula 12 in a collapsed configuration 20 under tension and in the operative position 22, the wire loop 18 extends from the blunt distal end 14 of the hollow cannula 12 and transitions into an expanded configuration 22.

Alternatively, the wire loop may have a natural collapsed configuration 20 and may be actuated to move into the expanded configuration 22.

In the expanded configuration 22, the loop of wire 18 adopts a leaf-like shape in which the region of the loop located at the opening 52, 152 at the distal end 14 of the cannula 12 is pinched to form the tip of the leaf-like shape. Suitably, the pinched end 24 is blunt to facilitate maneuvering of the wire loop 18 to the target location with minimal tissue damage.

The ends of wire loop 18 distal to the pinched end are anchored to a sliding member 26 which is housed and slides within the hollow cannula 12. Retaining the wire loop 18 within the hollow cannula 12 prior to engaging the fibrous connective tissue allows an operator to minimize the size of the entry point puncture and to position the cannula 12 under the skin of a patient without excessive damage to the surrounding tissue. Advantageously, this may reduce scarring and recovery time.

The hollow cannula 12 has a generally circular end cross section.

The distal end 14 of the cannula is blunt to enable the cannula to separate layers of tissue and/or muscle without puncturing or piercing the layers. This minimizes tissue damage when the cannula is maneuvered under the patient's skin.

In FIG. 1, the wire loop 18 is anchored to sliding member 26, which acts as an actuator. An end of the sliding member protrudes from the proximal end 16 of the hollow cannula 12 and can be gripped by an operator to manipulate the wire loop 18 between the retracted and operative positions.

Figures 2A, 2B:
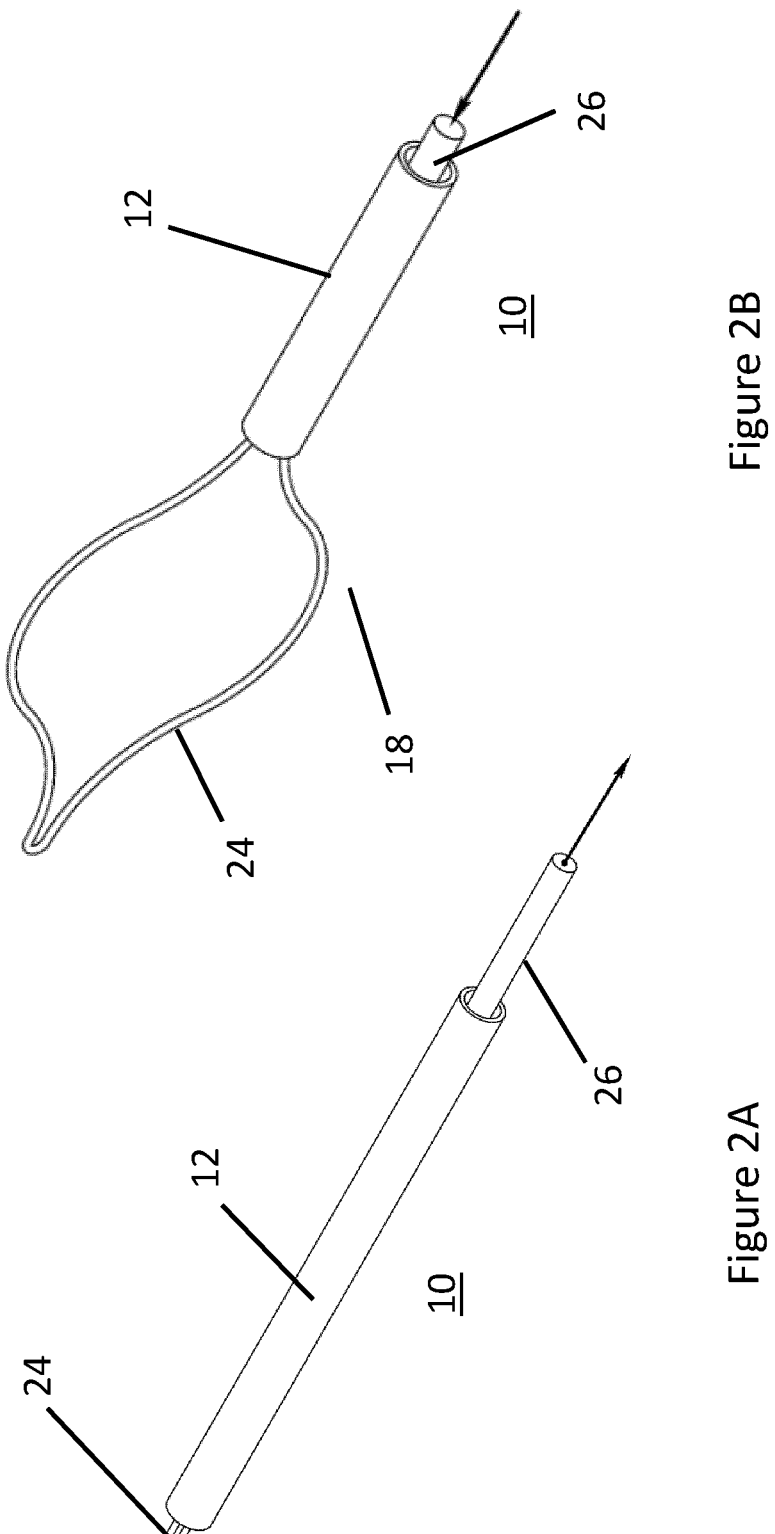
FIG. 2A is a perspective view of the device in FIG. 1A in the retracted position.
FIG. 2B is a perspective view of the device in FIG. 1A in the operative position.

From the retracted position 20, moving the sliding member 26 towards the blunt distal end 14 pushes the wire loop out of the opening 52 at the distal end and releases the wire loop from tension (see directional arrow in FIG. 2B). This transitions the wire loop 18 into its expanded configuration 22. Conversely, from the operative position, moving the sliding member 26 away from the blunt distal end 14 compresses the wire loop as it collapses into the cannula 12 (see directional arrow in FIG. 2A).

Figures 3A, 3B, 3C:
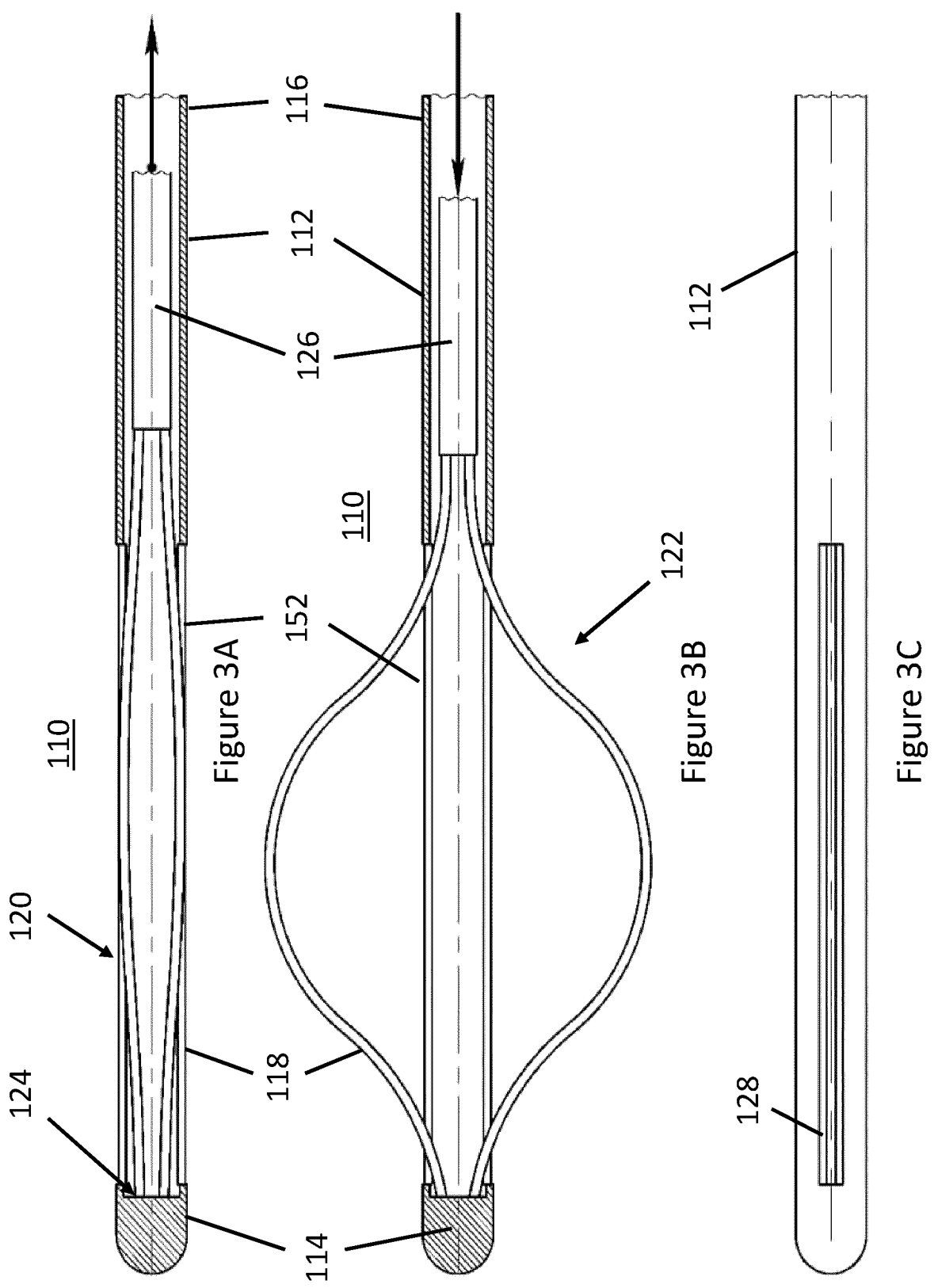
FIG. 3A is a cross-sectional side view of a device according to another form of the present disclosure in a retracted position.
FIG. 3B is a cross-sectional side view of the device in FIG. 3A in an operative position.
FIG. 3C is a plan view of the device in FIG. 3A in the retracted position.
Figures 4A, 4B:
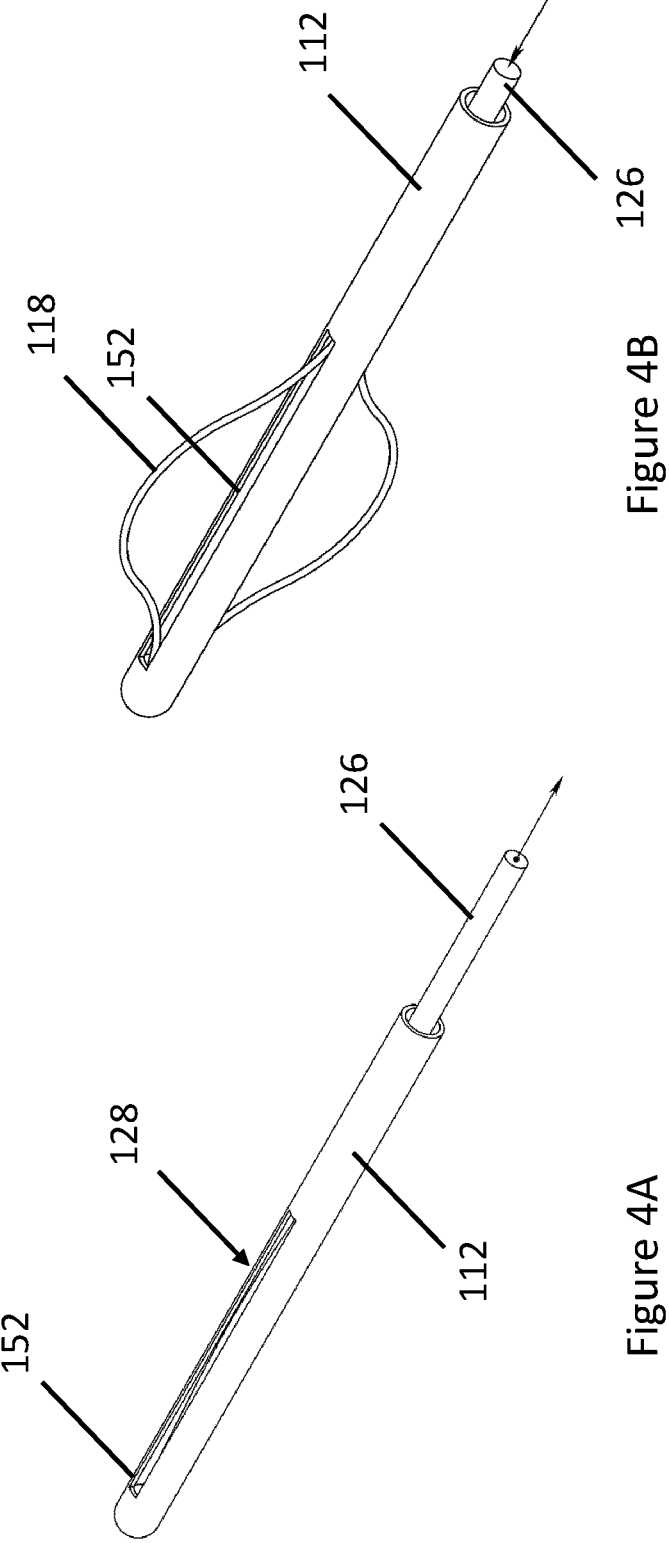
FIG. 4A is a perspective view of the device in FIG. 3A in the retracted position.
FIG. 4B is a perspective view of the device in FIG. 3A in the operative position.

Another embodiment of the disclosure is marked as 110 in FIGS. 3A/B and 4A/B.

The device 110 comprises a hollow cannula 112 configured to be pushed between or through layers of tissue, the hollow cannula 112 having a closed distal end 114 and a pair of apertures in the form of slots 128 that extend along the length of the cannula 112.

A user controllable breaking means, in the form of wire loop 118 is positioned within the hollow cannula 112.

In the retracted position 120, the wire loop 118 is housed within the hollow cannula 112 in a collapsed configuration 120 and in the operative position 122, the wire loop 118 expands outwardly from the slots 128 into the operative position to form a wing-like profile on opposing sides of the cannula 112. The cannula 112 provides structural support to the wire loop 118 when it is being manipulated under the skin of a patient. In contrast, the wire loop of device 10 is maneuvered under the skin of the patient unsupported and may be damaged (e.g., bent into an undesirable shape) if unusually rigid body structures are encountered during the manipulation. The slotted cannula also allows the wire loop 118 to be made from less rigid materials.

The ends of wire loop 118 are anchored to a sliding member 126, which is housed and slides within the hollow cannula 112. The pinched end 124 of the wire loop is diametrically opposed to the anchored end and is housed within closed distal end 114 of the cannula 112. Suitably, the pinched region 124 is attached to the closed end of the cannula 112.

As with the embodiment illustrated in FIGS. 1A/B and 2A/B, an end of the sliding member 126 protrudes from the proximal end 116 of the hollow cannula 112 and can be gripped by an operator to manipulate the wire loop 118 between the retracted and operative positions.

From the retracted position, moving the sliding member 126 towards the blunt closed distal end 114 compresses the wire loop 118 along the axis of the cannula. This causes the wire loop 118 to project outwardly from slots 128. Conversely, from the operative position, moving the sliding member 126 away from the blunt closed distal end 114 retracts the wire loop 118 into cannula 112, which may release the wire loop from tension.

Figure 5:
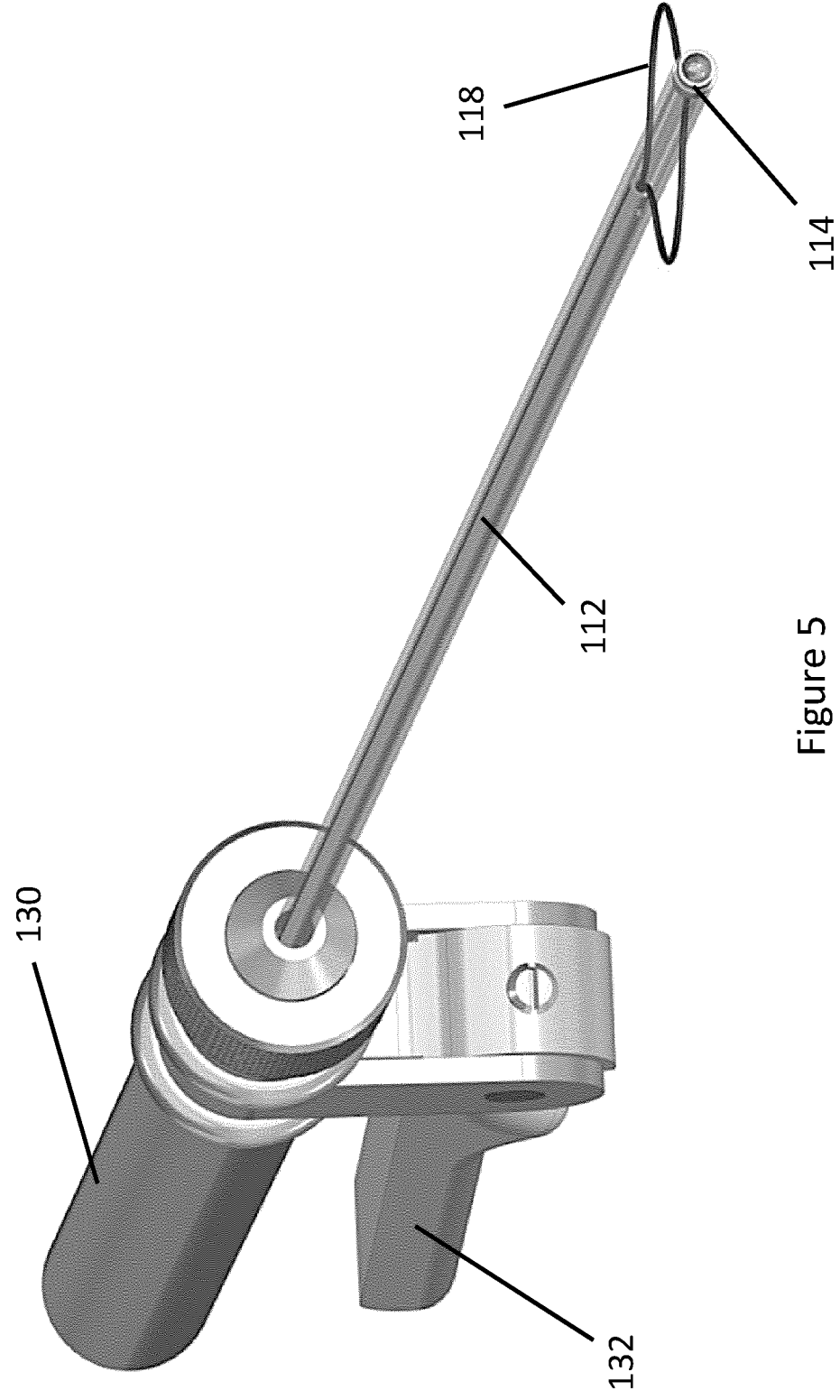
FIG. 5 is a perspective view of the device in FIGS. 3A/B and 4A/B including a handle.

In the embodiment illustrated in FIG. 5, the sliding member 126 is connected to handle 130, which includes an actuator in the form of squeeze grip 132. The device may be biased in the operative position 122 in which squeezing the grip 132 moves the wire loop 118 into the retracted position 120. Alternatively, the device may be biased in the retracted position 120 in which squeezing grip 132 moves the wire loop 118 into the operative position 122.

It can be appreciated that the embodiment illustrated in FIGS. 1A/1B and 2A/2B can also be connected to handle 130.

With regard to the embodiments described in the figures, the wire loop 18, 118 may be made of any suitable material that can repeatedly transition between the collapsed and expanded configurations 20, 120 and 22, 122, respectively, without fracturing. Appropriate materials include shape memory alloys such as nitinol, room temperature annealing materials such as lead or a lead alloy, ductile materials such as copper, iron or steel and alloys thereof. Other suitable materials include metals such as titanium and silver and alloys thereof, polymers such as nylon, polyethylene, polymethylmethacrylate, polycarbonate and composites thereof, and dental wire.

Suitably, the hollow cannula 12, 112 is rigid. However, it can be made from a material that allows it to bend into and be retained in a desired shape such as steel, or ductile material such as copper or iron.

Figures 6A, 6B, 6C, 6D:
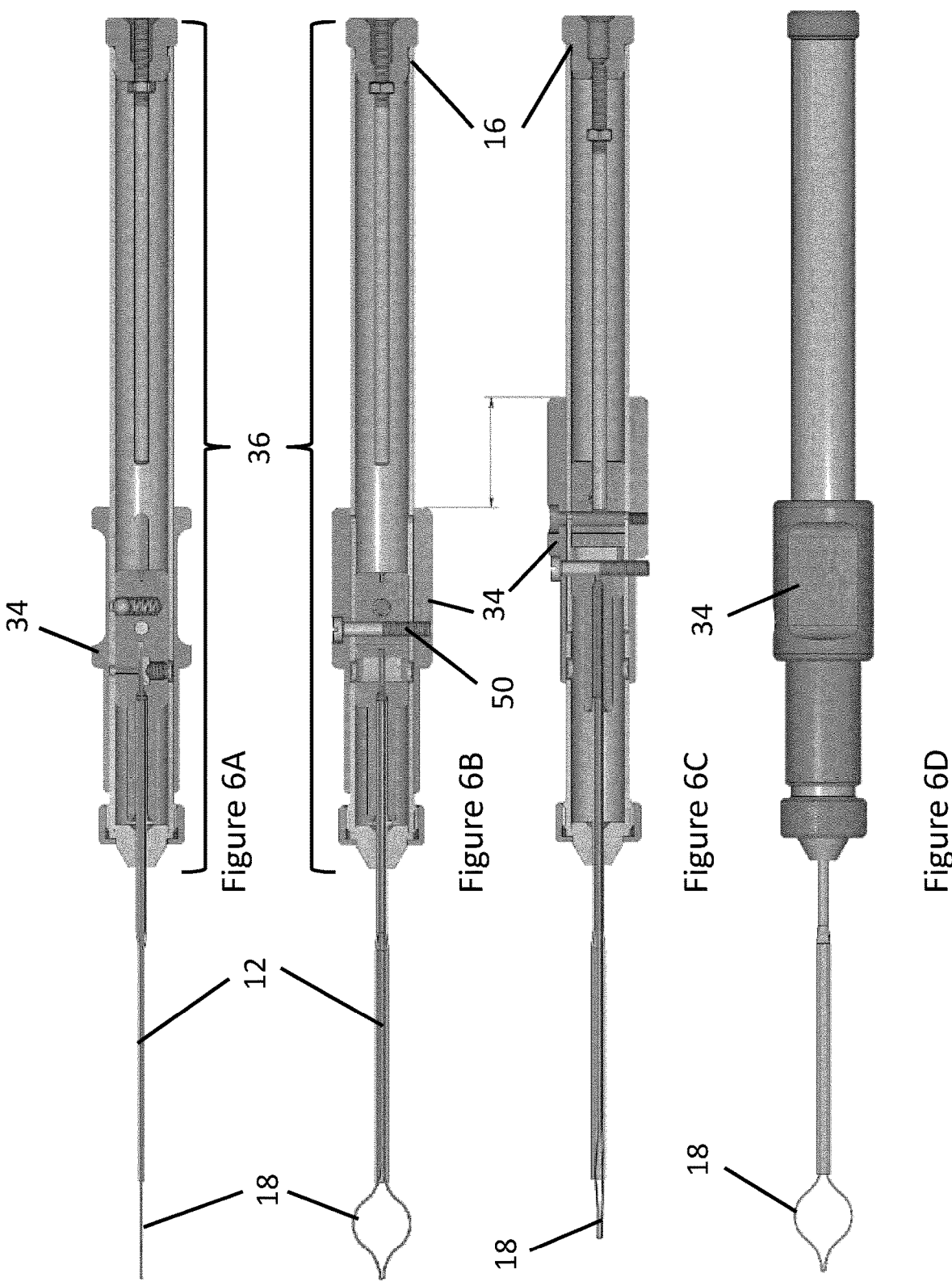
FIGS. 6A and 6B illustrate the device of FIG. 1B attached to a handle.
FIG. 6C illustrates the device of FIG. 1A attached to a handle.
FIG. 6D is a plan view of the device in FIG. 6B.

The embodiment illustrated in FIGS. 6A and 6B will now be used to demonstrate use of the device. In this embodiment, the hollow cannula 12 is attached to a handle 34 that is actuatable to move the breaking means 18 between the retracted and operative positions 20 and 22, respectively.

During a cellulite treatment procedure, if not already in its retracted position, the device 10 is moved into the retracted position 20 by sliding slider 34 of handle 36 towards the proximal end 16 (FIG. 6C). This forces wire loop 18, having a natural expanded configuration 22, into the hollow cannula 12 under tension.

After the skin 38 of the patient (comprising dimples 40) is prepared with antiseptics and local anesthesia, an entry puncture on the patient's skin is created (not shown; typically about 1-2 mm in diameter) and the hollow cannula 12 is inserted through the entry puncture point into the subcutaneous fat layer 42 (FIG. 7).

The cannula 12 is maneuvered under the patient's skin 36 to a target location into the direction A such that the blunt distal end 14 is positioned after a strand of fibrous connective tissue 44 (FIG. 7).

Slider 28 is slid within the hollow cannula towards the distal end 14. This moves the wire loop 18 out of the opening 52, 152 in the distal end 14 (FIG. 6C) which releases the wire loop from tension and causes it to transition from its collapsed configuration 20 (FIG. 6C) into its expanded configuration 22 (FIGS. 6A, 6B and 6D). During the transition, the pinched end 24 of the wire loop 18 leads the wire loop 18 into the subcutaneous fat layer past a strand of fibrous connective tissue 44 (FIG. 8). The blunt pinched end 24 of the wire loop 18 minimizes puncturing or cutting of tissue, including blood vessels 46, along the path travelled by the wire loop 18 to the target location.

A locking means, in the form of screw 50, is fastened in the operative position 22 to prevent the wire loop 18 from unintentionally being retracted into the cannula 12 (FIG. 6B).

The cannula 12 is then pulled along reverse direction B such that the wire loop 18 engages and stretches the strand of fibrous connective tissue 44 at least until a breaking point. Engaging the fibrous connective tissue strands 44 by withdrawing the wire loop 18 typically causes the wire loop 18 to reduce in size as the fibrous connective tissue strands 44 press against the curved sides of the wire loop 18 to generate a compressive force that is transverse to the axis of the cannula 12. The reduction in size of the wire loop reduces the likelihood of indiscreet tissue damage. Similarly, a more gradual angle of the breaking means also reduces the likelihood of indiscreet damage.

In contrast, if the fibrous connective tissue 44 was engaged by pushing the wire loop 18 against the strand of fibrous connective tissue, it is likely that the wire loop 18 would be compressed along the axis of the cannula 12. This would widen the wire loop 18, making it more likely to engage a larger area of surrounding tissue, and potentially to cause more indiscreet tissue damage.

Once the strand of fibrous connective tissue 44 breaks, the screw 50 is released and slider 34 is slid towards proximal end 16 to retract the wire loop 18 into the cannula 12 (FIG. 6C).

The cannula 12 is then maneuvered under the skin to another strand of fibrous connective tissue, and the procedure is repeated until the desired number of strands of fibrous connective tissue is broken to reduce or eliminate the dimpling of the epidermis 38 caused by cellulite or other conditions.

Advantageously, the procedure does not rely on a cutting means to sever the strands of fibrous connective tissue. This reduces the likelihood of tissue damage in the vicinity of the strands of fibrous connective tissue during movement of the cutting means towards the fibrous connective tissue. Having the breaking means 18 engage the fibrous connective tissue 44 during the pulling action also reduces tissue trauma compared to a method in which the blunt distal end 14 is positioned before the fibrous connective tissue strand 44 and the fibrous strand is engaged and broken by pushing the expanded wire loop 18 in direction A into the fibrous strand.

If necessary, the hollow cannula 12 can be bent into a desired shape to facilitate the procedure. This allows the shape of the hollow cannula 12 to be adapted to the contours of the body part of the patient, or a desired path under the patient's skin.

As a result, the present disclosure provides a device 10, 110 and a method for treating conditions where fibrous connective tissue contributes to formation of skin dimples that reduces tissue trauma.

In some embodiments, the device 10, 110 may include active elements which enhance the operation of the breaking means 18, 118 to break fibrous connective tissue threads 44. For example, in an embodiment, the actuator may include an electronic mechanism that triggers a repeated forward-backwards motion of the cannula body 12, 112 and the breaking means 18, 118 in the operative position 22, 122 to aid breaking of the fibrous adhesions 44. In some embodiments, the breaking means 18, 118 may be moved by the actuator in a backwards and forwards motion relative to the elongate body in the form of a cannula 12, 112. The frequency and length of movement may vary between embodiments and may also be stepwise. In this example, the actuator may be a small electric motor, for example similar to an electric toothbrush. In another example, the breaking means 18, 118 and/or the elongate body 12, 112 act as vibrating/pulsatile elements controlled by the electronic mechanism. For example, the actuator may be a vibrator, which may operate at high frequencies, for example similar to a dental cleaning pick. Turning the vibration on and off may be controlled by the operator, for example using a button on the handle 36, 130, such that the vibration is tuned on to transmit through the breaking means 18, 118 when this is engaged with the fibrous connective tissue 44 to encourage breaking. Suitably, the electronic mechanism is located in the handle 36, 130.

In another example, the breaking means 18, 118 of the device 10, 110 may include a plurality of breaking elements that are actuatable to move in a scissoring motion relative to each other along the axis of the elongate body to aid breaking of the fibrous adhesions 44. For example, the plurality of breaking elements (having blunt edges and rounded ends) may expand outwardly, like wings, and optionally be moved manually by the operator or by an electronic actuator to expand and contract to encourage breaking of any fibrous adhesions in contact with the breaking elements. As these elements have rounded and/or blunt edges, the fibrous adhesions are encouraged to break rather than be cut.

Although the embodiment discussed above and illustrated in the drawings shows a round cross section for the elongate body 12, 112, the elongate body 12, 112 may have a variety of cross-sectional profiles, which may be radially symmetrical or asymmetrical. Suitable cross-sectional profiles include circular, oval, polygonal, and rectangular profiles. In one embodiment, the elongate body has a radially asymmetrical cross-sectional profile such as an oval or flattened profile. This type of profile may also enable a tactile determination of the orientation of the breaking means by the user. The profile may also aid manipulation of the orientation of the breaking means in use—without needing to sight the breaking means 18, 118. In another embodiment, the surface of the elongate body 12, 112 may be marked to assist a user in visually determining the orientation of the breaking means 18, 118. In other embodiments, the handle 36, 130 may be shaped or marked to indicate the orientation of the breaking means 18, 118.

In the context of the present disclosure, the terms "fibrous adhesions" and "fibrous connective tissue" are used interchangeably and mean tightened/stiffened connective tissue, i.e., connective tissue, which has a reduced elasticity in comparison to corresponding "normal," or "healthy," or "non-stretched" connective tissue. As such the terms include, but are not limited to, tightened/stiffened connective tissue bands, connective tissue strands, connective tissue threads, and connective tissue sheaths considered causative for a cosmetic or medical condition including, but not limited to skin conditions, including cellulite, wrinkles, acne, burns or depressed skin-grafts, and/or nerve or blood vessel compression, including carpal tunnel syndrome or compartment syndrome and/or considered to present as the result of surgical treatment, trauma, scarring, and/or pregnancy.

In the claims which follow and in the preceding description of the disclosure, except where the context requires otherwise due to express language or necessary implication, the word "comprise" or variations such as "comprises" or "comprising" is used in an inclusive sense, i.e., to specify the presence of the stated features but not to preclude the presence or addition of further features in various embodiments of the disclosure.

Further, reference throughout this specification to "one embodiment," "some embodiments" or "an embodiment" means that a particular feature, structure or characteristic described in connection with the embodiment is included in at least one embodiment of the present disclosure. Thus, appearances of the phrases "in one embodiment," "in some embodiments" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

As used herein, unless otherwise specified the use of the ordinal adjectives "first," "second," "third," etc., to describe a common object, merely indicate that different instances of like objects are being referred to, and are not intended to imply that the objects so described must be in a given sequence, either temporally, spatially, in ranking, or in any other manner.

As used herein, the term "exemplary" is used in the sense of providing examples, as opposed to indicating quality. That is, an "exemplary embodiment" is an embodiment provided as an example, as opposed to necessarily being an embodiment of exemplary quality.

It is to be understood that, if any prior art publication is referred to herein, such reference does not constitute an admission that the publication forms a part of the common general knowledge in the art.

REFERENCE NUMERALS

10, 110 device
12, 112 elongate body, cannula
14, 114 distal end
16, 116 proximal end
18, 118 breaking means, wire loop
20, 120 retracted position, collapsed configuration
22, 122 operative position, expanded configuration
24, 124 pinched end

26, 126 sliding member
128 slots
130 handle
132 actuator, squeeze grip
34 slider
36 handle
38 skin, epidermis
40 dimple
42 subcutaneous fat layer
44 fibrous material, fibrous connective tissue, fibrous adhesion
46 blood vessels
48 muscle
50 locking means, screw
52, 152 opening The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled.

The invention claimed is:

1. A device for performing a cosmetic or medical procedure, comprising:
   a hollow elongate body having a body wall with at least one opening, wherein the at least one opening is proximal from a distal end of the hollow elongate body; and
   one or more user controllable breaking means that are positioned within the hollow elongate body,
   wherein each breaking means comprises (a) at least one breaking element made of a non-cutting wire comprising a shape-memory alloy, and (b) a distal end portion,
   wherein the at least one breaking element is actuatable to move the wire between a retracted position and an operative position,
   wherein when in the retracted position, the wire is housed within the hollow elongate body in a collapsed configuration and when in the operative position, the wire projects outwardly through the at least one opening in the body wall in an expanded configuration suitable to break a strand of fibrous material while the distal end portion of the breaking means remains housed within the hollow elongate body,
   wherein the wire is biased towards the expanded configuration and is placed under tension within the hollow elongate body when in the collapsed configuration, and
   wherein the wire is configured to break a strand of fibrous connective tissue by tensioning or stretching the strand away from the hollow elongate body until complete or partial rupture of the strand, the wire having strength in the expanded configuration to break the strand of fibrous connective tissue by tensioning the strand to and/or past a point of rupture.

2. The device according to claim 1, wherein the breaking means is slidable within the hollow elongate body such that the breaking means slides within the hollow elongate body when moving the wire from the retracted position into the operative position.

3. The device according to claim 1, wherein the hollow elongate body comprises a sliding member slidingly movable within the hollow elongate body and wherein the breaking means is attached to the sliding member.

4. The device according to claim 3, wherein the hollow elongate body and/or the sliding member is configured such as to restrict rotation of the breaking means relative to the hollow elongate body when the wire is in the expanded configuration.

5. The device according to claim 1, wherein the wire, in the expanded configuration, assumes the shape of a hoop, a half-hoop, an oval, an ellipse, a diamond, a rectangle, or a square or assumes a leaf-like shape.

6. The device according to claim 1, wherein the wire expands along one plane when transitioning from the collapsed configuration to the expanded configuration.

7. The device according to claim 1, wherein the wire is movable in discrete increments between the retracted position and the operative position such that expansion of the wire into the expanded configuration occurs in corresponding increments.

8. The device according to claim 1, wherein the device comprises a plurality of the breaking elements.

9. The device according to claim 1, wherein the cosmetic or medical procedure is a treatment of fibrous adhesions associated with medical or cosmetic skin conditions, including cellulite, wrinkles, acne, burns or depressed skin-grafts; surgical treatment; trauma; scarring; pregnancy; and/or nerve or blood vessel compression, including carpal tunnel syndrome or compartment syndrome.

10. A method of operating a device comprising a hollow elongate body having a proximal end, a distal end, a body wall with at least one opening that is proximal from the distal end, and one or more breaking means retained under tension in a retracted position within the hollow elongate body, wherein the breaking means comprises (a) at least one breaking element made of a non-cutting wire comprising a shape-memory alloy, and (b) a distal end portion, and the wire is biased towards an expanded configuration and configured to break a strand of fibrous material by tensioning or stretching the strand away from the hollow elongate body until complete or partial rupture of the strand, the wire having strength in the expanded configuration to break the strand of fibrous material by tensioning the strand to and/or past a point of rupture, the method comprising:
   positioning the hollow elongate body to provide the breaking means at a target location; and
   actuating the breaking means to move the wire from a retracted position to an operative position in which the wire projects outwardly through the at least one opening in the body wall in the expanded configuration while the distal end portion of the breaking means remains housed within the hollow elongate body, and
   wherein, when moving from the retracted position to the operative position, the wire transitions from a collapsed configuration to the expanded configuration having a strength suitable to break the strand of fibrous material.

11. The method according to claim 10, further comprising performing a cosmetic or medical procedure using the device, the one or more breaking means being user controllable, wherein the at least one breaking element is actuatable to move the wire between the retracted position and the operative position, and wherein when in the retracted position, the wire is in the collapsed configuration, and when in the operative position, the wire is in the expanded configuration suitable to break the strand of fibrous connective tissue.

12. A method of operating a device comprising a hollow elongate body having a proximal end, a distal end, a body wall with at least one opening that is proximal from the distal end, and a breaking means retained in a retracted position under tension within the hollow elongate body, wherein the breaking means comprises (a) at least one breaking element made of a non-cutting wire comprising a shape-memory alloy, and (b) a distal end portion, and the wire is biased towards an expanded configuration and configured to break a strand of fibrous material by tensioning or stretching the strand away from the hollow elongate body until complete or partial rupture of the strand, the wire having strength in the expanded configuration to break the strand of fibrous material by tensioning the strand to and/or past a point of rupture, the method including:

creating an entry point puncture in a patient;

inserting the breaking means with the wire in the retracted position through the entry point puncture and maneuvering the breaking means with the wire in the retracted position through tissue of the patient to a target location having a strand of fibrous connective tissue, wherein in the retracted position the wire is in a collapsed configuration;

actuating the breaking means to transition the wire into an operative position in which the wire projects outwardly through the at least one opening in the body wall in the expanded configuration while the distal end portion of the breaking means remains housed within the hollow elongate body;

manipulating the device such as to break the strand of fibrous connective tissue using the breaking means to push the strand of fibrous connective tissue away from the hollow elongate body until complete or partial rupture of the strand; and actuating the breaking means to transition the wire into the retracted position.

* * * * *